United States Patent [19]

Gruber et al.

[11] 4,181,575

[45] Jan. 1, 1980

[54] COMPOSITION AND METHOD FOR THE DETERMINATION OF CHOLESTEROL

[75] Inventors: Wolfgang Gruber, Tutzing-Unterzeismering; Gunter Lang; Michael Nelboeck-Hochstetter, both of Tutzing; Peter Röeschlau, Seeshaupt; Hans Seidel, Tutzing; Detlef von Hoerschelmann, Wielenbach, all of Fed. Rep. of Germany

[73] Assignee: Boehringer Mannheim GmbH, Mannheim-Waldhof, Fed. Rep. of Germany

[21] Appl. No.: 842,001

[22] Filed: Oct. 13, 1977

[30] Foreign Application Priority Data

Oct. 29, 1976 [DE] Fed. Rep. of Germany ....... 2649749

[51] Int. Cl.$^2$ ............................................. G01N 31/14
[52] U.S. Cl. ..................................................... 435/11
[58] Field of Search .................... 195/103.5 R, 99, 63, 195/66 R

[56] References Cited

U.S. PATENT DOCUMENTS 3,907,642  9/1975  Richmond .................... 195/103.5 R

FOREIGN PATENT DOCUMENTS 579148  8/1976  Switzerland ........................... 195/66 R

OTHER PUBLICATIONS

Marcus, et al., "Induction and Purification of α- and β-Hydroxy Steroid Dehydrogennses", *J. Biol. Chem.* vol. 218, (1956) pp. 661-673.

Talalay, et al., "Specificity, Kinetics, and Inhibition of α- and β-Hydroxysteroid Dehydrogennses", *J. Biol. Chem.*, vol. 218 (1956) pp. 675-690.

Parmentier et al., "Mechanism of Brohydrogenation of Cholesterol to Coprostanol by Eubacterium ATCC 21408", *Biochem. Biophys. Acta,* vol. 348 (1974) pp. 279-284.

Curish, "Cholesterol Oxidase, A Literature Review", Beckman Instruments, Inc. 1969.

Klingenberg, Methods of Enzymatic Analysis by H. U. Bergmeyer, 1974 pp. 2045-2059.

*Primary Examiner*—Thomas G. Wiseman
*Attorney, Agent, or Firm*—Sprung, Felfe, Horn, Lynch & Kramer

[57] ABSTRACT

In a process for the determination of total or bound cholesterol by liberating any bound cholesterol using cholesterol esterase and simultaneously or subsequently determining the liberated cholesterol and any initially free cholesterol with a cholesterol reacting enzyme, the improvement comprising using as the cholesterol reacting enzyme an NAD or NADP-dependent cholesterol dehydrogenase obtained from an anaerobic microorganism, e.g., Eubacterium sp. ATCC 21408, or from mammalian tissue, e.g., liver.

13 Claims, No Drawings

COMPOSITION AND METHOD FOR THE DETERMINATION OF CHOLESTEROL

The present invention is concerned with a process and reagent for determining total and bound cholesterol.

German Pat. No. 2,506,712 describes a process for determining total or bound cholesterol by liberating bound cholesterol with cholesterol esterase and determining the free cholesterol with a cholesterol-reacting enzyme. As cholesterol-reacting enzyme, there is disclosed cholesterol oxidase which, in the presence of atmospheric oxygen, converts cholesterol into cholestenone, with the formation of hydrogen peroxide.

A special advantage of the above-described process is that it permits a completely enzymatic determination of cholesterol in biological material where cholesterol is usually present not only in free but also in bound form as esters. By means of this completely enzymatic determination, the previously usual at least two-stage determination, in which the saponification of the ester had to be carried out in a separate step, is considerably simplified.

In analytical and clinical determinations, use is very frequently made of methods which, in coupled reactions, finally lead to the reduction of nicotinamide-adenine dinucleotide (NAD) or nicotinamide-adenine dinucleotide phosphate (NADP), with the formation of NADH or NADPH, since the latter reaction can be monitored especially easily in conventionally used photometers. However, the above-described completely enzymatic cholesterol ester determination can be coupled only in a very complicated and laborious manner with subsequent enzymatic reactions yielding, finally, the measureable NADH or NADPH.

We have now found that it is possible to overcome this difficulty and to provide a completely enzymatic determination for cholesterol esters or mixtures of cholesterol esters and free cholesterol which makes possible not only the direct measurement of the NADH or NADPH concentration without inserted reactions, and thus additional expense and additional possibilities of error, but also the determination of the cholestenone formed as in the case of the previously known completely enzymatic process.

The present invention comprises a process for the determination of total or bound cholesterol by liberating bound cholesterol with a cholesterol esterase and simultaneously or subsequently determining the liberated cholesterol with a cholesterol-reacting enzyme, by employing as the cholesterol-reacting enzyme an NAD- or NADP-dependent cholesterol dehydrogenase obtained from an anaerobic micro-organism or from mammalian liver.

This process is preferably carried out according to the above-mentioned German Pat. No. 2,506,712, using a cholesterol esterase obtained from micro-organisms. However, the process can also be carried out with the use of a cholesterol esterase obtained from pancreas or liver, the use of the latter enzyme for this purpose already being known from German Pat. No. 2,224,132.

The present invention is based upon the discovery of an NAD- or NADP-dependent cholesterol dehydrogenase in anaerobic micro-organisms. In general, this enzyme can be found in those anaerobes which are able to dehydrogenate a 3-β-OH group-containing steroid present in a nutrient medium used for culturing the anaerobes, to give the corresponding enone. We have found that Eubacterium sp. ATCC 21408 is especially useful for obtaining this enzyme.

However, instead of the above-described microbial enzyme, it is also possible to use a cholesterol dehydrogenase obtained from mammalian liver.

In the process according to the present invention, cholesterol esterase and NAD- or NADP-dependent cholesterol dehydrogenase are preferably added simultaneously to the sample to be determined, preferably as mixture of the enzymes. However, it is, of course, also possible to add the enzymes successively and, for example, first to allow the saponification of the cholesterol ester by the cholesterol esterase from micro-organisms to run to completion before the cholesterol dehydrogenase to be employed according to the present invention is added. In this case, a cholesterol esterase from micro-organisms is preferably used in order to ensure complete ester splitting even in the absence of the enzyme which further reacts the cholesterol.

The NAD- or NADP-dependent cholesterol dehydrogenase employed according to the present invention dehydrogenates cholesterol with the formation of cholestenone and transfers the hydrogen split off to NAD or NADP with the formation of NADH or NADPH which, as mentioned above, can be measured directly in a photometer. In this way, there is provided an especially simple method of determination which does not require a subsequent measurement reaction. The photometric determination of NADH or NADPH is well known and does not need to be further described here.

However, if desired, the process according to the present invention also makes it possible to determine the cholestenone formed, the cholestenone determination preferably being carried out by adding a hydrazine derivative which reacts with the keto group of the cholestenone to form a hydrazone. For this purpose, 2,4-dinitrophenylhydrazine is preferably used because, with cholestenone, it forms a hydrazone which can easily be measured in a photometer at 405 nm.

The process according to the present invention can be carried out at a pH value of from 4.5 to 8.5 and preferably of from 5 to 8. The concentration of the buffer solution used is not critical, good results being achieved at a concentration of from 0.05 to 0.8 M, the range of from 0.1 to 0.6 M being preferred.

If desired, in carrying out the process according to the present invention, in addition to the buffer, there can also be added a stabilizing agent and/or a surface-active agent for preventing the appearance of turbidity or undesired activation. The stabilizing agent used can be any one of those usually employed for enzymes or for NAD or NADP but the use thereof is not essential: it is also possible to work without the addition of a surface-active agent, especially when it is certain that the cholesterol concentration in the sample to be investigated is not so high that an appearance of turbidity, which could disturb the optical test, is to be feared.

For obtaining the NAD- or NADP-dependent enzyme to be used according to the present invention, it is necessary to culture the micro-organisms under strictly anaerobic conditions. The exclusion of oxygen can be achieved by adding an agent for removing oxygen, such as methylene blue, and maintaining an inert gas atmosphere. As inert gas, there can be used, for example, nitrogen, hydrogen, noble gases or mixtures thereof, a mixture of nitrogen and hydrogen having proved to be especially favorable.

An appropriate nutrient medium for culturing strictly anaerobic mirco-organisms has, for example, the following composition, referred to 1 liter of medium:

20 to 80 g. homogenized, fresh brain
5 to 25 g. yeast extract
5 to 25 g. casamino acids
1 to 5 g. sodium chloride
1 to 3 g. an alkali metal thioglycolate
0.5 to 5 g. cholesterol or other 3-$\beta$-OH-steroid
0.5 to 1.5 g. sodium bicarbonate
0.2 to 1 g. L-cystine
5 to 10 ml. 0.05% aqueous methylene blue solution.

The medium should have a substantially neutral pH value. Before inoculation with the micro-organisms, the medium must be freed from oxygen by heating. All manipulations, including the purification, must also be carried out in an inert atmosphere.

The period of culturing varies, depending upon the micro-organism used. For the above-mentioned Eubacterium spec. ATCC 21408, incubation for 30 to 40 hours at 37° to 40° C. has proved to be advantageous. At the end of this culturing period, the medium assumes a gel-like appearance. By centrifuging and resuspension in buffer, preferably a phosphate buffer of pH 6 to 8, the biomass can be concentrated to about 20%.

Subsequent digestion of the biomass is preferably carried out mechanically and not by chemical agents. Ultrasonic digestion or grinding with fine glass pearls or the like has proved to be advantageous. These and other appropriate mechanical digestion methods are well known and do not need to be described here in detail. The digestion is preferably carried out in the absence of a surface-active agent.

Insoluble components are centrifuged off from the digestion material obtained. Although the crude extract so obtained can be used directly for the process according to the present invention, the enzyme is preferably concentrated by precipitation with a conventional precipitation agent, such as ammonium sulphate. When using ammonium sulphate, it is preferably added up to a concentration of 3.1 M. The precipitate obtained can be then used directly for the determination or can be further purified, for example, possibly by column chromatography, molecular sieve chromatography or other known biochemical purification methods.

If, instead of the microbial enzyme, there is used one from mammalian liver, then an analogous purification process can be employed, the fraction precipitated between 30 and 50% ammonium sulphate saturation preferably being employed for the determination.

When culturing an anaerobic micro-organism, to the nutrient there is expediently added, as 3-$\beta$-OH-group-containing steroid, one of the substances mentioned in Germam Pat. No. 2,456,586 or a mixture thereof.

The present invention also provides a reagent for carrying out the above-described process which, in one embodiment, comprises cholesterol esterase, NAD- or NADP-dependent cholesterol dehydrogenase, NAD or NADP, a buffer and optionally a stabilizing agent and/or a surface-active agent.

According to a further embodiment, the reagent comprises cholesterol esterase, NAD- or NADP-dependent cholesterol dehydrogenase, a system for the determination of cholestenone, a buffer and optionally a stabilizing agent and/or a surface-active agent. The system for the determination of cholestenone is preferably a hydrazine derivative which reacts with a keto group to form a hydrazone formation, 2,4-dinitrophenylhydrazine being especially preferred for the determination of cholestenone.

The preferred composition of such a reagent comprises 0.04 to 4 U cholesterol esterase, 0.04 to 50 U NAD- or NADP-dependent cholesterol dehydrogenase and 10 to 100 mM NAD or NADP or 0.5 to 10 mM of a hydrazine derivative per 2 ml. of reagent. If the reagent contains a surface-active agent, such as hydroxypolyethoxydodecane, then the concentration thereof is preferably between 0.1 and 1%, corresponding to 0.002 to 0.02 ml., per 2 ml. of reagent, i.e. the amount of reagent usually employed in a test batch.

The process and reagent according to the present invention enables a very rapid and complete determination of bound and free cholesterols to be carried out, especially in biological samples, such as serum, blood and the like. An especial advantage is than no additional measurement reactions have to be coupled on and the determination can be carried out directly with the use of a simple conventional photometer.

The following Examples are given for the purpose of illustrating the present invention:

EXAMPLE 1

Eubacterium spec. ATCC 21408, a strictly anaerobic micro-organism, is inoculated on to a medium of the following composition:

per liter:
50 g. fresh calf brain (homogenized)
15 g. yeast extract (DIFCO)
15 g. casamino acids
2.5 g. sodium chloride
2.0 g. sodium thioglycolate
2.0 g. cholesterol
1.0 g. sodium bicarbonate
0.5 g. L-cystine
7.5 g. 0.05% methylene blue solution
(pH value 6.9–7.1; immediately before inoculation, the medium is freed from oxygen by heating; all manipulations, including purification, take place in an isolated vessel in an atmosphere of nitrogen/hydrogen).

After 30 to 40 hours incubation at 37° to 40° C., the medium has become gel-like. By centrifuging and resuspension in 0.1 M phosphate buffer (pH 7.5), the biomass is concentration 1:5 and then digested in a Sorvall mill (+$\phi$0.25 mm. glass pearls 1:1, 3 min., switch position 4).

Ammonium sulphate is added to the centrifuged crude extract up to a concentration of 3.1 M; the precipitate formed is separated off and taken up in 0.05 M phosphate buffer (pH 7.5) and applied to a column containing a molecular sieve material based on cross-linked dextran. The column is eluted with 0.05 M phosphate buffer (pH 7.5) and the fractions containing the active material are combined and lyophilized.

EXAMPLE 2

0.02 ml. Serum are added to 1.0 ml. 0.1 M potassium phosphate buffer (pH 7.5) which contains 0.4% hydroxypolyethoxydodecane and $\lambda$, 5 mM NAD (NADP). After the addition of 0.02 ml. (2 U) cholesterol esterase solution, as well as 0.05 ml. of the cholesterol dehydrogenase solution of Example 1, followed by incubation for 30 minutes at 25° C., 2 ml. 1 mM 2,4-dinitrophenylhydrazine in 10% hydrochloric acid solution are pipetted into the reaction mixture. After further incubation at 25° C. for 30 minutes, 3.0 ml. water are added to the reaction solution, followed by measurement against a reagent blank (water is added instead of serum) at 405 nm in an appropriate photometer.

Evaluation is carried out by comparison with a code-termined cholesterol standard. The measurement of a typical sample gives 147 mg. cholesterol/100 ml. serum. A comparison determination with a commercially-available reagent based on cholesterol oxidase gives 149 mg. cholesterol/100 ml. serum.

EXAMPLE 3

1.89 ml. 0.5 M Phosphate buffer (pH 7.5), which contains 0.4% hydroxypolyethoxydodecane, is mixed with 0.1 ml. 13 mM NADP solution and 0.02 ml. serum and introduced into a cuvette. Extinction $E_1$ is read off at 365 nm in an appropriate photometer. After the addition of 0.02 ml. (2 U) cholesterol esterase solution and 0.05 ml. cholesterol dehydrogenase solution according to Example 1, the mixture is incubated at 25° C. in a water-bath.

After 30 minutes, extinction $E_2$ is read off. The extinction difference $E_2 - E_1 = E$ is used for the calculation, which is carried out according to the Lambert-Beer Law. Measurement of a typical sample gives 150 mg. cholesterol/100 ml. serum. A comparison determination with a commercially-available reagent based on cholesterol oxidase gives 149 mg. cholesterol/100 ml. serum.

EXAMPLE 4

Preparation of a Cholesterol Dehydrogenase from Rat Liver

Rat liver is homogenized with the 3 fold amount of 0.25 M aqueous saccharose solution and centrifuged at 80,000 g. The supernatant obtained is adjusted to pH 7.0 and brought to 30% saturation with ammonium sulphate and the precipitate is centrifuged off. The supernatant is mixed with an equal volume of saturated ammonium sulphate solution and the precipitate obtained centrifuged off and dialysed against distilled water.

The dialysate is adjusted with 1M phosphate buffer to 0.2 M phosphate content and pH 6.0 and mixed with 0.1 volume aluminium oxide gel. The suspension is then centrifuged, the precipitate is discarded and the supernatant is mixed with ammonium sulphate up to 2.7 M. The precipitate thus obtained is centrifuged off and dissolved at c=10 ml. The enzyme solution obtained contains about 0.005 U/ml.

When using 1 ml. of this solution for carrying out the process according to Examples 2 and 3, instead of the there used dehydrogenase preparation, practically the same results are obtained.

It will be understood that the specification and examples are illustrative but not limitative of the present invention and that other embodiments within the spirit and scope of the invention will suggest themselves to those skilled in the art.

What is claimed is:

1. In a cholesterol assay wherein a sample suspected of containing bound cholesterol is treated with cholesterol esterase to liberate cholesterol and the liberated cholesterol is subsequently or simultaneously measured by its enzymatic conversion to cholesterase using a cholesterol reacting enzyme, the improvement comprises using as the cholesterol reacting enzyme a NAD- or NADP-dependent cholesterol dehydrogenase obtained from either an anaerobic microorganism or from a mammalian liver.

2. Improvement as claimed in claim 1 wherein the cholesterol esterase and the NAD- or NADP-dependent cholesterol dehydrogenase are added simultaneously to the sample to be determined.

3. Improvement as claimed in claim 1 wherein the cholesterol dehydrogenase used is obtained from Eubacterium sp. ATCC 21408.

4. Improvement as claimed in claim 1 wherein the cholesterol dehydrogenase is obtained by the mechanical digestion of the anaerobic micro-organism in the absence of surface-active agents, followed by separation of the insoluble components.

5. Improvement as claimed in claim 1 wherein a purified NAD- or NADP-dependent cholesterol dehydrogenase preparation precipitated by the addition of ammonium sulfate up to a concentration of 3.1 M is used.

6. Improvement as claimed in claim 1 wherein the cholesterol dehydrogenase from an anaerobic microorganism which has been cultured in oxygen-free atmosphere in a nutrient medium containing a thioglycolate and a 3-β-OH group containing steroid is used.

7. Improvement as claimed in claim 1 wherein the cholestenone formed by action of the cholesterol reacting enzyme on the liberated cholesterol is determined as a measure of the cholesterol initially present.

8. Improvement as claimed in claim 1 wherein NAD or NADP is also added and the NADH or NADPH formed, upon formation of cholestenone by action of said cholesterol reacting enzyme on said liberated cholesterol, by transfer of the hydrogen released thereby to said NAD or NADP, is determined as a measure of the initial cholesterol content.

9. Composition for the determination of total or bound cholesterol which comprises cholesterol esterase and NAD- or NADP-dependent cholesterol dehydrogenase and a buffer.

10. Composition as claimed in claim 9 which comprises cholesterol esterase, NAD- or NADP-dependent cholesterol dehydrogenase, a system for the determination of cholestenone and a buffer.

11. Composition as claimed in claim 10 wherein the system for the determination of cholestenone is a hydrazine derivative which reacts with a keto group to form a hydrazone.

12. Composition as claimed in claim 11 wherein the hydrazine derivative is 2,4-dinitrophenylhydrazine.

13. Composition as claimed in claim 9 additionally containing at least one of a stabilizing agent and a surface-active agent.

* * * * *